United States Patent
Guevremont et al.

(10) Patent No.: US 6,774,360 B2
(45) Date of Patent: Aug. 10, 2004

(54) FAIMS APPARATUS AND METHOD USING CARRIER GAS OF MIXED COMPOSITION

(75) Inventors: Roger Guevremont, Gloucester (CA); Randy Purves, Gloucester (CA); David Barnett, Orleans (CA)

(73) Assignee: National Research Council Canada, Ottawa (CA)

(*) Notice: Subject to any disclaimer, the term of this patent is extended or adjusted under 35 U.S.C. 154(b) by 10 days.

(21) Appl. No.: 10/220,604
(22) PCT Filed: Mar. 14, 2001
(86) PCT No.: PCT/CA01/00310
§ 371 (c)(1), (2), (4) Date: Sep. 3, 2002
(87) PCT Pub. No.: WO01/69646
PCT Pub. Date: Sep. 20, 2001

(65) Prior Publication Data
US 2003/0057369 A1 Mar. 27, 2003

Related U.S. Application Data
(60) Provisional application No. 60/189,085, filed on Mar. 14, 2000.

(51) Int. Cl.[7] .................................................. H01J 49/40
(52) U.S. Cl. ...................... 250/288; 250/281; 250/282; 250/286
(58) Field of Search ................................. 250/281, 282, 250/286, 288, 287

(56) References Cited

U.S. PATENT DOCUMENTS

| | | | |
|---|---|---|---|
| 5,106,468 A | 4/1992 | Chimenti | |
| 5,283,199 A | 2/1994 | Bacon, Jr. et al. | |
| 5,420,424 A * | 5/1995 | Carnahan et al. | 250/287 |
| 5,520,424 A | 5/1996 | Carnahan et al. | |
| 5,723,861 A | 3/1998 | Carnahan et al. | |
| 5,736,739 A | 4/1998 | Uber et al. | |
| 5,763,876 A | 6/1998 | Pertinarides et al. | |
| 5,789,745 A | 8/1998 | Martin et al. | |
| 5,801,379 A | 9/1998 | Kouznetsov | |
| 5,869,831 A | 2/1999 | De La Mora et al. | |
| 5,955,886 A * | 9/1999 | Cohen et al. | 324/464 |
| 6,041,734 A | 3/2000 | Raoux et al. | |
| 6,124,592 A * | 9/2000 | Spangler | 250/287 |
| 6,162,709 A | 12/2000 | Raoux et al. | |
| 6,323,482 B1 | 11/2001 | Clemmer et al. | |
| 6,495,823 B1 * | 12/2002 | Miller et al. | 250/286 |

(List continued on next page.)

FOREIGN PATENT DOCUMENTS

| | | |
|---|---|---|
| RU | 2105298 | 2/1998 |
| WO | WO 00/63949 A1 | 10/2000 |
| WO | WO 01/22049 A2 | 3/2001 |

OTHER PUBLICATIONS

U.S. patent application Ser. No. 09/762,238, Guevremont et al., not published.
Carr et al., "Plasma Chromatography", (1984), Plenum Press, New York.
Mason et al., "Transport Properties of Ions in Gases", (1988), Wiley, New York.

(List continued on next page.)

*Primary Examiner*—John R. Lee
*Assistant Examiner*—Paul M. Gurzo
(74) *Attorney, Agent, or Firm*—Freedman & Associates

(57) ABSTRACT

A method and an apparatus is disclosed for selectively transmitting ions with a FAIMS analyzer in which a flow of carrier gas of a mixed composition is provided. Ions that are transmitted at a same combination of applied potentials when a first carrier gas is provided are in certain cases transmitted at different combinations of applied potentials when a second other carrier gas having a different composition is provided.

19 Claims, 15 Drawing Sheets

U.S. PATENT DOCUMENTS

| | | |
|---|---|---|
| 6,504,149 B2 | 1/2003 | Guevremont et al. |
| 6,512,224 B1 | 1/2003 | Miller et al. |
| 6,621,077 B1 | 9/2003 | Guevremont et al. |
| 6,639,212 B1 | 10/2003 | Guevremont et al. |
| 6,653,627 B2 | 11/2003 | Guevremont et al. |
| 2001/0030285 A1 | 10/2001 | Miller et al. |
| 2003/0020012 A1 | 1/2003 | Guevremont et al. |
| 2003/0038235 A1 | 2/2003 | Guevremont et al. |
| 2003/0057367 A1 | 3/2003 | Guevremont et al. |
| 2003/0089847 A1 | 5/2003 | Guevremont et al. |
| 2003/0150985 A1 | 8/2003 | Guevremont et al. |
| 2003/0213904 A9 | 11/2003 | Guevremont et al. |

OTHER PUBLICATIONS

Buryakov et al., "A New Method of Separation of Multi-Atomic Ions by Mobility at Atmospheric Pressure using a High–Frequency Amplitude–Asymmetric Strong Electric Field", Int. J. Mass Spectrom. Ion Processes, No. 128, pp. 143–148, (1993), Elsevier Science Publishers B.V.

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper #96–009, pp. 87–95, (1996), Framingham, MA, USA.

Riegner et al., "Qualitative Evaluation of Field Ion Spectrometry for Chemical Warfare Agent Detection", Proceedings of the 45th ASMS Conference on Mass Spectrometry and Allied Topics, Palm Springs, California, pp. 473, (1997).

Purves et al., "Mass Spectrometric Characterization of a High–Field Asymmetric Waveform Ion Mobility Spectrometer", Review of Scientific Instruments, vol. 69, No. 12, pp. 4094–4105, (Dec. 1998), American Institute of Physics.

Guevremont et al., "Atmospheric Pressure Ion Focusing in a High–Field Asymmetric Waveform Ion Mobility Spectrometer", Review of Scientific Instruments, vol. 70, No. 2, pp. 1370–1\383, (Feb. 1999), American Institute of Physics.

Krylov, "A Method of Reducing Diffusion Losses in a Drift Spectrometer", Tech. Phys., vol. 44, No. 1, pp. 113–116, (1999), American Institute of Physics.

* cited by examiner

FAIMS APPARATUS AND METHOD USING CARRIER GAS OF MIXED COMPOSITION

This application claims the benefit of U.S. Provisional application No. 60/189,085 filed Mar. 14, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U. Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, $V_1$, lasting for a short period of time $t_2$ and a lower voltage component, $V_2$, of opposite polarity, lasting a longer period of time $t_1$. The waveform is synthesized such that the integrated voltage-time product, and thus the field-time product, applied to the plate during each complete cycle of the waveform is zero, for instance $V_1 t_2 + V_2 t_1 = 0$; for example +2000 V for 10 $\mu$s followed by −1000 V for 20 $\mu$s. The peak voltage during the shorter, high voltage portion of the waveform is called the "dispersion voltage" or DV in this disclosure.

During the high voltage portion of the waveform, the electric field causes the ion to move with a transverse y-axis velocity component $v_1 = K_h E_{high}$, where $E_{high}$ is the applied field, and $K_h$ is the high field ion mobility under ambient electric field, pressure and temperature conditions. The distance traveled is $d_1 = v_1 t_2 = K_h E_{high} t_2$, where $t_2$ is the time period of the applied high voltage. During the longer duration, opposite polarity, low voltage portion of the asymmetric waveform, the y-axis velocity component of the ion is $v_2 = K E_{low}$, where K is the low field ion mobility under ambient pressure and temperature conditions. The distance traveled is $d_2 = v_2 t_1 = K E_{low} t_1$. Since the asymmetric waveform ensures that $(V_1 t_2) + (V_2 t_1) = 0$, the field-time products $E_{high} t_2$ and $E_{low} t_1$ are equal in magnitude. Thus, if $K_h$ and K are identical, $d_1$ and $d_2$ are equal, and the ion is returned to its original position along the y-axis during the negative cycle of the waveform, as would be expected if both portions of the waveform were low voltage. If at $E_{high}$ the mobility $K_h > K$, the ion experiences a net displacement from its original position relative to the y-axis. For example, positive ions of type A travel farther during the positive portion of the waveform, for instance $d_1 > d_2$, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of $K_h$ to K is similarly different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of $K_h$ to K. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained. It is a significant limitation of early FAIMS devices, which used electrometer detectors, that the identity of peaks appearing in the CV spectrum are other than unambiguously confirmed solely on the basis of the CV of transmission of a species of ion. This limitation is due to the unpredictable, compound-specific dependence of $K_h$ on the electric field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30 1995, B. L. Carnahan and A. S. Tarassove disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focussing of ions by the use of asymmetric waveforms has been discussed above. For completeness, the behavior of those ions that are not focussed within the analyzer region of a cylindrical geometry FAIMS is described here, briefly. As discussed previously, those ions having high field ion mobility properties that are other than suitable for focussing under a given set of DV, CV and geometric conditions will drift toward one or another wall of the FAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focussed, for example at DV 2500 volts, CV –11 volts in a given geometry, it would seem reasonable to expect that the ion is also focussed if the polarity of DV and CV are reversed, for instance DV of –2500 volts and CV of +11 volts. This, however, is not observed and in fact the reversal of polarity in this manner creates a mirror image effect of the ion-focussing behavior of FAIMS. The result of such polarity reversal is that the ions are not focussed, but rather are extremely rapidly rejected from the device. The mirror image of a focussing valley, is a hill-shaped potential surface. The ions slide to the center of the bottom of a focussing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform, yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focussing behavior described above, except that the ion-focussing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focussing. If the CV and DV are suitable for the focussing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focussing effect of the electric fields of the FAIMS mechanism. This is an example of a three-dimensional atmospheric pressure ion trap, as disclosed in a copending PCT application in the name of R. Guevremont and R. Purves, the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a part thereof; electrodes that are spheres or a part thereof; electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in $K_h$ at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a small orifice leading into the vacuum system of a mass spectrometer.

Additionally, the resolution of a FAIMS device is defined in terms of the extent to which ions having similar mobility properties as a function of electric field strength are separated under a set of predetermined operating conditions. Thus, a high-resolution FAIMS device transmits selectively a relatively small range of different ion species having similar mobility properties, whereas a low-resolution FAIMS device transmits selectively a relatively large range of different ion species having similar mobility properties. The resolution of FAIMS in a cylindrical geometry FAIMS is compromised relative to the resolution in a parallel plate geometry FAIMS because the cylindrical geometry FAIMS has the capability of focusing ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution.

Note that, while the above discussion refers to the ions as being "captured" or "trapped", in fact, the ions are subject to continuous 'diffusion'. Diffusion always acts contrary to focussing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

The refereed published scientific literature concerning the behavior of ions at high electric fields specifies that the behavior of a particular ion in a mixture of two gases is predicted, at low E/N, where E is the electric field strength and N is the number density of the gas, from the behavior of the ion in the two gases each in pure form. This is consistent with the theory of ion mobility, and the kinetic theory of gases. At high E/N a small deviation from this predicted value occurs because the effective temperature of the ion in each of the pure gases is slightly different, whereas the ion can only experience one finite effective temperature in the mixture of gases. These adjustments are discussed by Viehland and Mason (At. Data. Nucl. Data Tables 60, 37 (1995) and 21, 113 (1984) and 17, 177 (1976)). These corrections to the ideal behavior are small.

Prior art FAIMS devices typically use a carrier gas comprising a purified flow of one of nitrogen, oxygen and air. Recent experimental work with FAIMS, however, has indicated that in some cases there are very significant deviations from the predicted and obvious behavior of ions in mixtures of gases. These deviations have major implications on the application of FAIMS, since in some cases the use of a mixture of gases will make separations of certain ions feasible, where the separation is other than possible with the normal selection of pure gases. It would be advantageous to provide a method and an apparatus for extending the ion separation capability of a FAIMS device using a flow of carrier gas of an adjustable mixed composition.

OBJECT OF THE INVENTION

In order to overcome these and other limitations of the prior art, it is an object of the present invention to provide a high field ion mobility spectrometer that is supplied by a source of carrier gas having a variable but known composition.

In order to overcome these and other limitations of the prior art, it is an object of the present invention to provide a high field ion mobility spectrometer in which the composition of a carrier gas is adjustable by adding at least a second other gas to the initial carrier gas.

SUMMARY OF THE INVENTION

In accordance with the invention there is provided an apparatus for separating ions, comprising a high field asymmetric waveform ion mobility spectrometer, including:

an analyzer region comprising:

two electrodes, for providing an electric field therebetween resulting from an application of an asymmetric waveform to at least one of the electrodes in order to affect ion mobility, and for allowing at least a gas to pass therebetween; and, at least a gas inlet for introducing a first gas and a second other gas into the analyzer region, the first gas and the second other gas providing a predetermined mixture of gases within the analyzer region.

In accordance with the invention there is provided an apparatus for separating ions, comprising a high field asymmetric waveform ion mobility spectrometer, including:

an analyzer region comprising:

two electrodes, for providing an electric field therebetween resulting from an application of an asymmetric waveform to at least one of the electrodes in order to affect ion mobility, and for allowing at least a gas to pass therebetween;

a first gas inlet in fluid communication with a first gas source for receiving a flow of a first gas; and, a second gas inlet in fluid communication with a second gas source for receiving a flow of a second other gas; and, a mixing chamber disposed between the first and second gas inlets and the analyzer region, the mixing chamber separately in fluid communication with each one of the first and second gas inlets and the analyzer region for, in use, receiving a flow of the first gas from the first gas inlet and a flow of the second other gas from the second gas inlet, the mixing chamber further for providing at least a flow of gas having a predetermined composition, including the first gas and the second other gas, to the analyzer region.

In accordance with the invention there is provided a method for separating ions, comprising the steps of:

a) providing two electrodes including a first electrode and a second electrode;

b) providing an asymmetric waveform and a direct-current compensation voltage, to at least one of the two electrodes to form an electric field therebetween, the field for effecting a difference in net displacement between ions in a time of one cycle of the applied asymmetric waveform for effecting a separation of the ions by forming a subset thereof;

c) providing a carrier gas having a predetermined composition including at least two different chemical components through the electric field; and, d) transporting ions through the electric field in a direction approximately transverse to the electric field, wherein the two different chemical components act in conjunction with the electric field to effect a separation of the ions.

BRIEF DESCRIPTION OF THE DRAWINGS

FIG. 10b shows a mass spectrum obtained by analyzing the selectively transmitted ions corresponding to −12.3 volts CV in FIG. 10a;

FIG. 10c shows a mass spectrum obtained by analyzing the selectively transmitted ions corresponding to −15.5 volts CV in FIG. 10a.

DETAILED DESCRIPTION OF THE INVENTION

Figure 1:
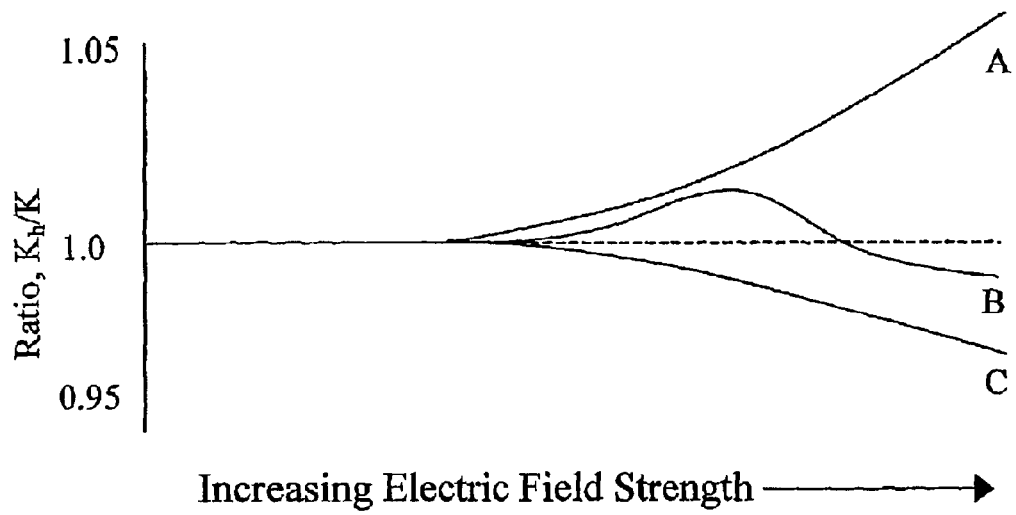
FIG. 1 shows three possible examples of changes in ion mobility as a function of the strength of an electric field.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility $K_{1,low}$ is other than separated in a FAIMS device from a second type A ion having a second different low field mobility $K_{2,low}$, if under the influence of high electric field strength, the ratio $K_{1,high}/K_{1,low}$ is equal to the ratio $K_{2,high}/K_{2,low}$. Interestingly, however, this same separation is achieved using conventional ion mobility spectrometry, which is based on a difference in ion mobilities at low applied electric field strength.

Figure 2A:
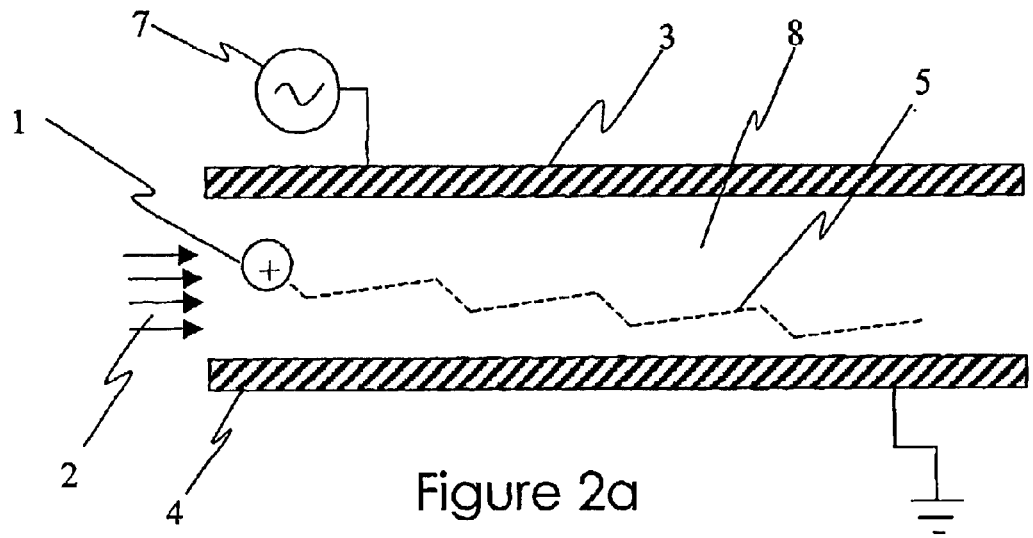
FIG. 2a illustrates the trajectory of an ion between two parallel plate electrodes under the influence of the electrical potential V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential, while the other plate 3 has an asymmetric waveform described by V(t), applied to it. The peak voltage applied during the waveform is called the dispersion voltage (DV), as is shown in FIG. 2b.

Figure 2B:
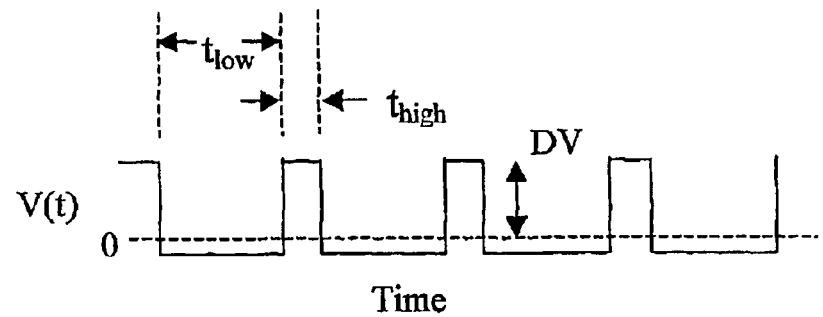
FIG. 2b shows an asymmetric waveform described by V(t)

Referring still to FIG. 2b, the waveform is synthesized so that the electric fields during the two periods of time thigh and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during $t_{high}$ and $t_{low}$ are no longer identical. Within an analyzer region defined by a space 8 between the first and second spaced apart electrode plates, 3 and 4, respectively, the ion 1 experiences a net displacement from its original position relative to the plates 3 and 4 as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of $K_h$ to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

Figure 3:
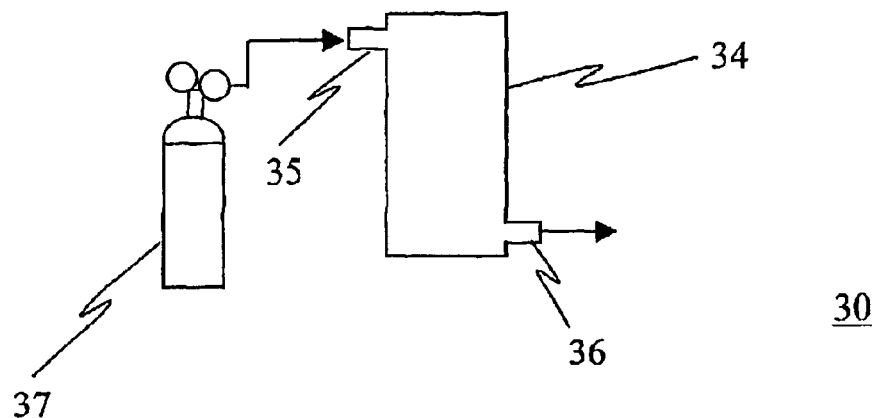
FIG. 3 shows a prior art FAIMS device using a single component carrier gas.

Referring to FIG. 3, a FAIMS apparatus according to the prior art is shown generally at 30. Ions produced in an ionization source (not shown) are provided to a FAIMS analyzer 34, the FAIMS analyzer 34 including a gas inlet 35 and a gas outlet 36, the gas inlet 35 and the gas outlet 36 for providing, in use, a flow of a carrier gas through the FAIMS analyzer 34. The carrier gas is provided from an external source, such as for example a compressed gas cylinder 37. A detection means (not shown), for instance an electrometer ion detector, is also provided for detecting the selectively transmitted ions. Additionally, an electrical controller (not shown) is provided for applying a dispersion voltage and compensation voltage to produce the electric fields within the FAIMS analyzer 34 for separating ions on the basis of the FAIMS principle.

Figure 4:
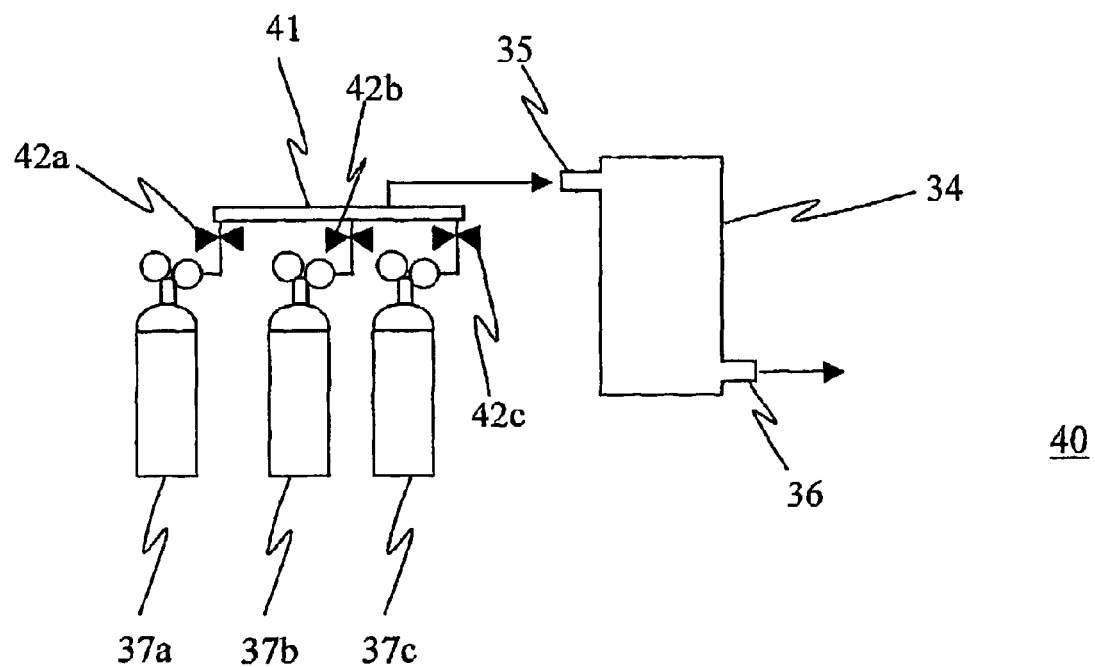
FIG. 4 shows a FAIMS device using a carrier gas of variable composition, according to the present invention.

Referring to FIG. 4, a FAIMS apparatus according to the present invention is shown generally at 40. Ions produced in an ionization source (not shown) are provided to a FAIMS analyzer 34, the FAIMS analyzer 34 including a gas inlet 35 and a gas outlet 36, the gas inlet 35 and the gas outlet 36 for providing, in use, a flow of a carrier gas through the FAIMS analyzer 34. The carrier gas is provided from an external source, for instance a gas manifold 41 connected to a series of compressed gas cylinders shown at 37a, 37b and 37c in FIG. 4. Valves 42a, 42b and 42c are provided for adjusting a flow of gas from cylinders 37a, 37b and 37c, respectively, into the gas manifold 41. Valves 42a, 42b and 42c are one of manually and electronically actuated. Of course, the number of compressed gas cylinders that is actually provided varies in dependence upon the requirements of the user of each system. Optionally, a gas source other than a compressed gas cylinder is connected to the manifold, for example one of a vessel for providing a gaseous product of a chemical reaction and an in-house gas supply line. Further optionally, the FAIMS analyzer 34 has a plurality of gas inlets, each inlet for providing a gas flow to a mixing chamber (not shown) internal to the FAIMS analyzer 34. A detection means (not shown), for instance an electrometer ion detector, is provided for detecting the selectively transmitted ions. Optionally, other alternative ion detection means are employed, for instance a mass spectrometric detector. The geometry of the FAIMS analyzer 34 is other than critical to the operation of the present invention. The FAIMS analyzer 34 shown in FIG. 4 is optionally selected from the group of FAIMS analyzers including: an n-electrode parallel plate FAIMS (n≧2); an n-electrode FAIMS with curved electrode plates (n≧2); a cylindrical geometry FAIMS device; and, a dome-terminus cylindrical geometry FAIMS device. The only requirement placed upon FAIMS analyzer 34 is that an electrical controller (not shown) applies a combination of dispersion voltage and compensation voltage to at least an electrode of the analyzer to for separating ions on the basis of the FAIMS principle.

In operation, ions are produced by the ionization source (not shown). The nature of the ionization source is determined in dependence upon the sample under investigation. For instance, an electrospray ionization source is used to produce ions from samples in the liquid phase. The ions are carried from the electrospray ionization source by the dc bias applied to a powered electrode of the FAIMS analyzer 34 and by a flow of carrier gas. A determined combination of dispersion voltage and compensation voltage is applied to at least an electrode of the FAIMS analyzer 34 to produce at least an electric field for selectively transmitting ions therethrough. For achieving the desired separation of ions, a carrier gas of a predetermined composition is provided through the gas inlet 35 of the FAIMS analyzer 34. At least a portion of the carrier gas being directed through the regions of strong electric fields, such that the transmitted ions interact with at least a component of the carrier gas during a period of time of at least one cycle of the applied asymmetric waveform. The composition of the carrier gas is controlled by setting an appropriate flow rate for each component of the carrier gas mixture to a mixing chamber, such as a gas manifold 41 external to the FAIMS analyzer 34. Optionally, a single source, for instance a lecture bottle, for providing a carrier gas of a predetermined composition is connected directly to the gas inlet 35. The selectively transmitted ions are detected using an appropriate detection means (not shown). For example, an electrometer detector is used, however more preferably a mass spectrometric detection system for unambiguously identifying the transmitted ions is used.

Figure 5A:
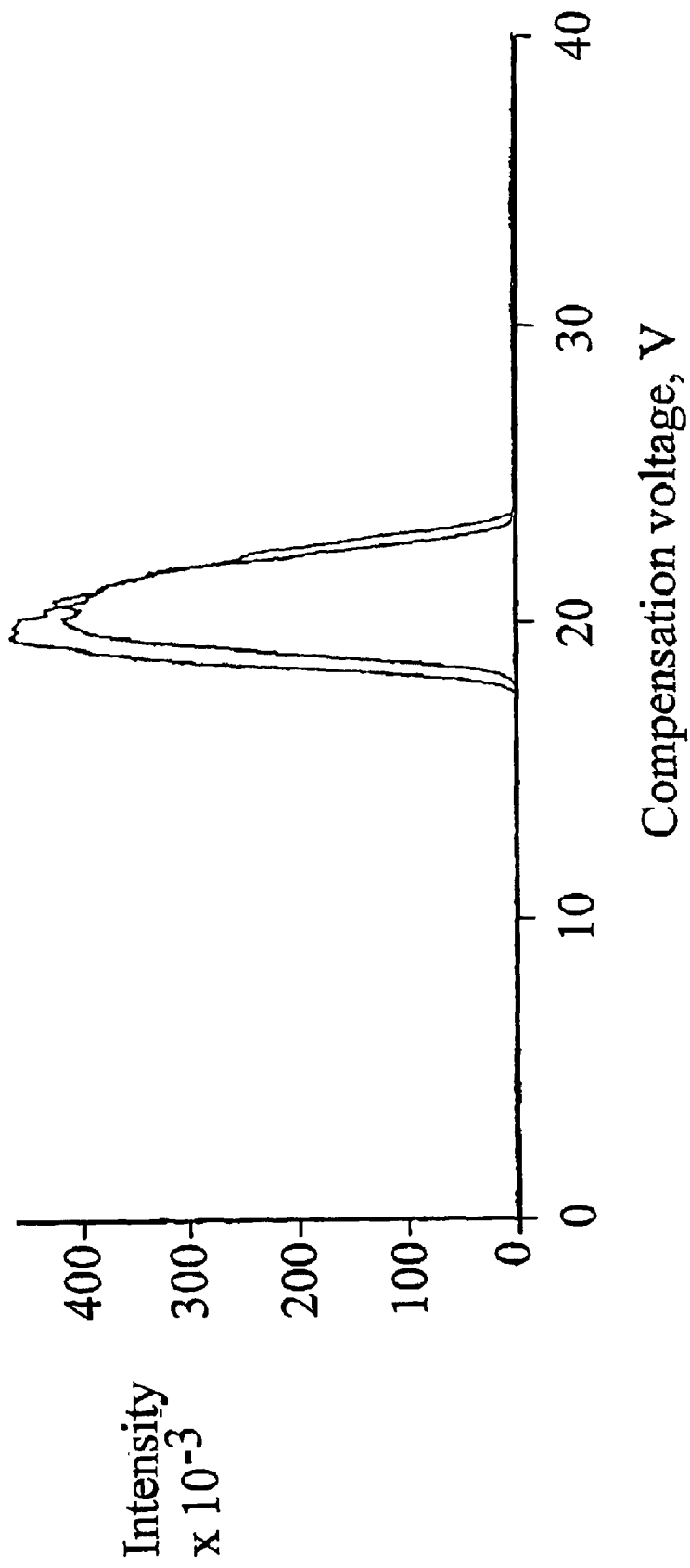
FIG. 5a shows a FAIMS CV spectrum of a sample of bromide ions obtained using pure argon carrier gas.
Figure 5B:
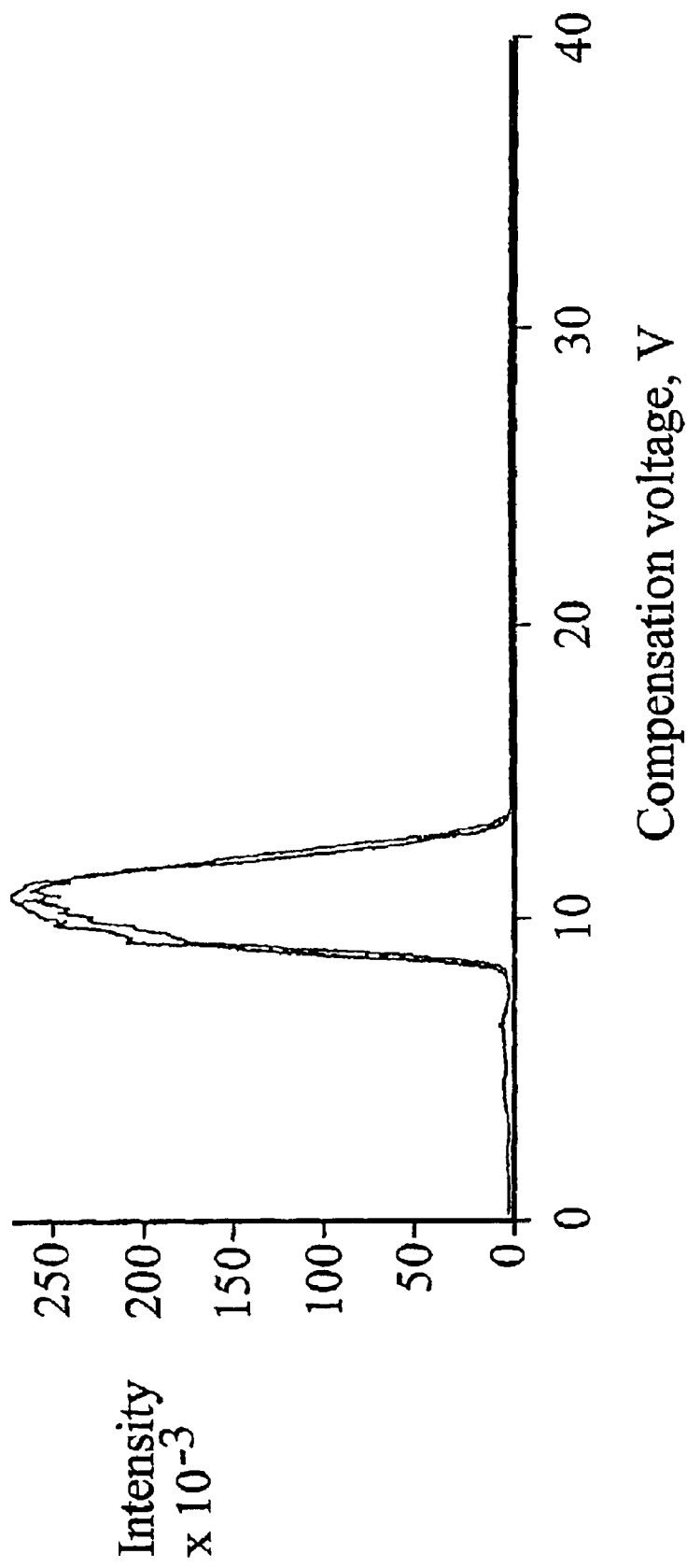
FIG. 5b shows a FAIMS CV spectrum of a sample of bromide ions obtained using pure carbon dioxide carrier gas.
Figure 5C:
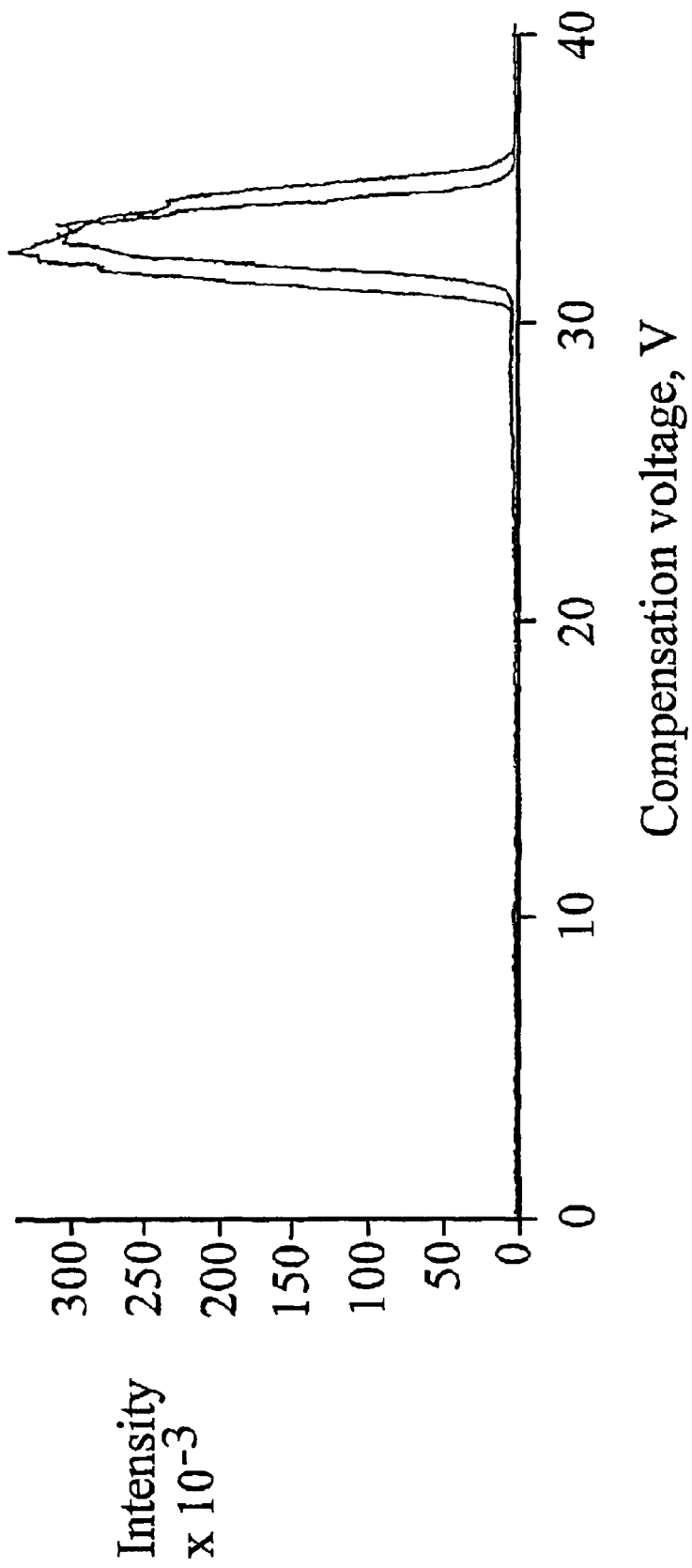
FIG. 5c shows a FAIMS CV spectrum of a sample of bromide ions obtained using a mixed argon and carbon dioxide carrier gas.

Referring to FIGS. 5a, 5b and 5c, shown are three compensation voltage spectra of the m/z 79 and m/z 81 isotopes of the negatively charged bromide ion. The three spectra were collected under identical conditions, but with different carrier gas composition. The CV spectrum of FIG. 5a was collected using argon gas, the CV spectrum of FIG. 5b was collected using carbon dioxide gas, and the CV spectrum of FIG. 5c was collected using a mixture of argon gas and carbon dioxide gas. Conventional knowledge of the high-field mobility of bromide would predict that the high-field mobility of bromide should appear midway between the mobility in argon and in carbon dioxide. In other words, it is expected that the bromide ion should appear at a CV value intermediate between that shown in FIG. 5a and FIG. 5b. In the CV spectrum that is actually observed using a mixture of argon and carbon dioxide, for instance as shown in FIG. 5c, the compensation voltage differs significantly from any value intermediate between those observed using the pure gases. The results shown in FIG. 5c are other than predictable from theory or from the data shown in FIGS. 5a and 5b. Nevertheless, an understanding of the principles of FAIMS does permit a reasonable hypothesis, which explains this phenomenon and which is consistent with the experiments performed using different carrier gas compositions. Of course, such a hypothesis is not to be taken as a statement of absolute certainty that the proposed explanation is the correct one.

Ions are separated in FAIMS in dependence upon differences in the mobility of the ion during the application of the high and low fields across the analyzer region of FAIMS. In a pure, contaminant-free gas, the high- and low-field mobilities are consequences of the interaction between the ion and the neutral gas molecules during collisions. At high field the collisions are more vigorous, and as a consequence slightly different interactions between the ion and the neutral gas molecules are manifested relative to the low field conditions. In a gas that contains contaminant molecules, the situation is less well defined since the ion may form transient, weakly bound complexes with the contaminant molecules. The ratio $K_h/K$ for the transient complex may be different from that of the parent ion, and as a result the behavior of the ion in FAIMS becomes more difficult to visualize. At one extreme a condition in which the complex between the ion and the contaminant molecule will exist during the low-field portion of the applied waveform, and the complex will dissociate during the high-field portion of the waveform because the ion is dragged through the bath gas with sufficient energy that the weakly bound contaminant molecule is stripped away from the ion. Therefore, in every cycle of the waveform there is a significant difference in the mobility of the ion, as a complex at low field, and as a bare ion at high field. This enhances the CV at which the ion appears. This is an observed consequence of the addition of traces of water vapor to the carrier gas flow.

Figure 6:
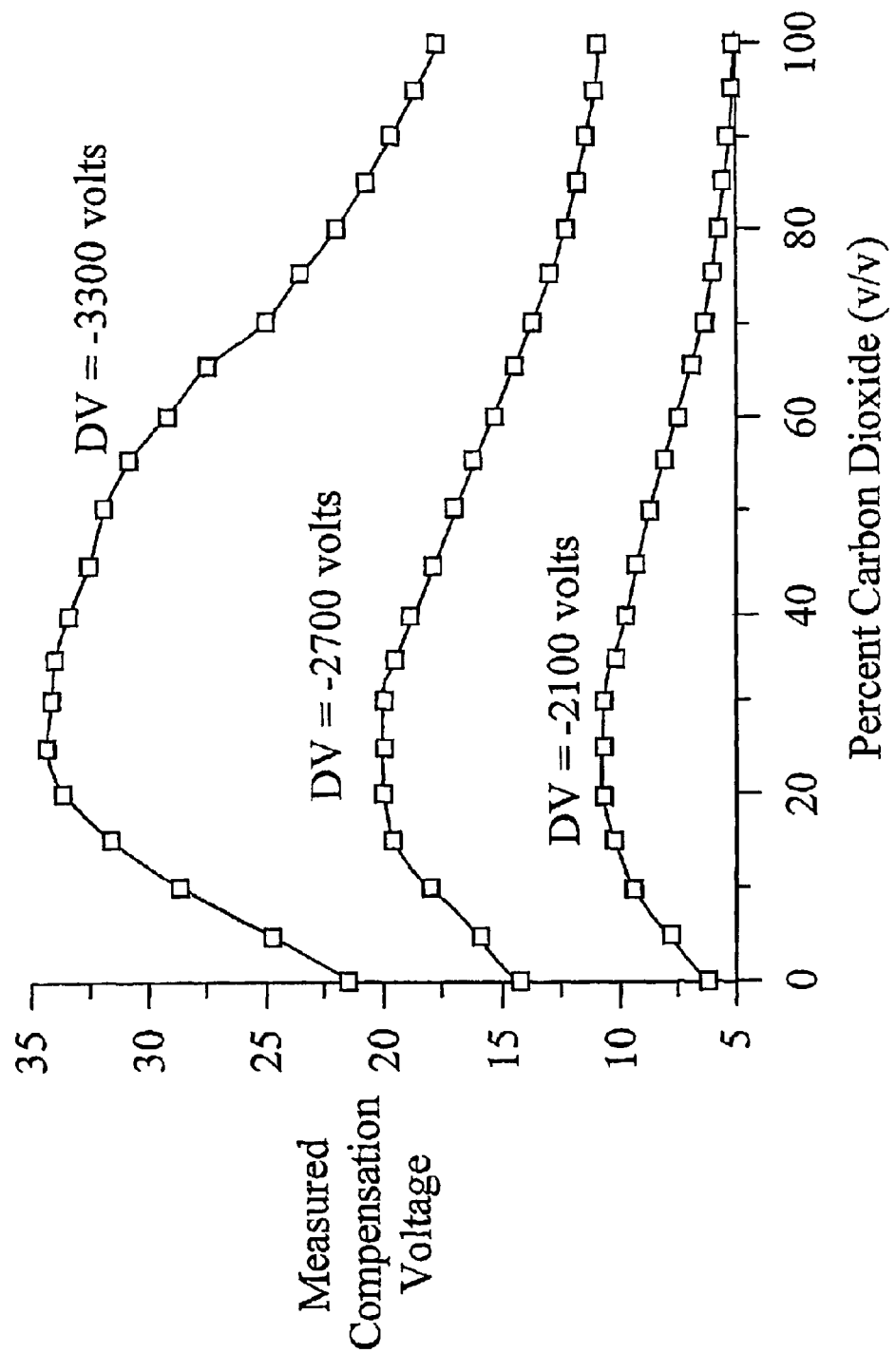
FIG. 6 shows experimental data illustrating the effect of the addition of carbon dioxide on the CV spectrum of $HSO_4^-$ at various DV voltages in FAIMS using nitrogen bath gas.

An experiment is easily performed with carbon dioxide, rather than with water vapor, to allow relatively larger, and more easily quantifiable, quantities of gas to be used. Carbon dioxide is known to form weak complexes with many ions. Referring to FIG. 6, shown is a plot of the experimental data for measurements of the CV for transmission of the negatively charged $HSO_4^-$ ion for a series of experimental conditions including various gas compositions from 0% to 100% carbon dioxide in nitrogen, and for three different DV, wherein the FAIMS device is operated in N1 mode. For example, at DV −3300 volts the $HSO_4^-$ ion is transmitted through FAIMS at about 22 volts in pure nitrogen and at about 17 volts in pure carbon dioxide. It is clear that at 25% carbon dioxide in nitrogen, at DV −3300 volts, the transmission of $HSO_4^-$ does not occur at a CV between 22 and 17 volts, but is actually transmitted at about 34 volts. Similar results are also shown in FIG. 6 for the application of DV −2700 and DV −2100 volts.

The data trends described with reference to FIG. 6 are explained in light of the formation and dissociation of complexes in a dynamic way during the application of the asymmetric waveform to the FAIMS apparatus. The complex formed of $HSO_4^-$ with carbon dioxide is very weakly bound, but the rate of formation of the complex is enhanced by the very high numbers of carbon dioxide molecules in a gas that has a substantial, for instance 10% by volume, carbon dioxide component. During application of the low voltage, low field, portion of the asymmetric waveform there is a tendency for the formation of a complex, or of complexes, between $HSO_4^-$ and carbon dioxide molecules. As noted above, this weakly bound complex then dissociates during the high-field portion of the waveform because the motion of the ion contributes to an apparent increase in temperature, which in turn shifts the equilibrium towards the dissociation of the complex. This combined formation/dissociation cycle is repeated every cycle of the asymmetric waveform and the apparent value of the compensation voltage is enhanced relative to that observed in either pure gas. The kinetics of the formation and destruction of such complexes, with the assumption that equilibrium is reached in a time frame short relative to the changes in the applied voltages via the asymmetric waveform suggest that this explanation of the reasons for the results shown in FIG. 6 is feasible.

Figure 7:
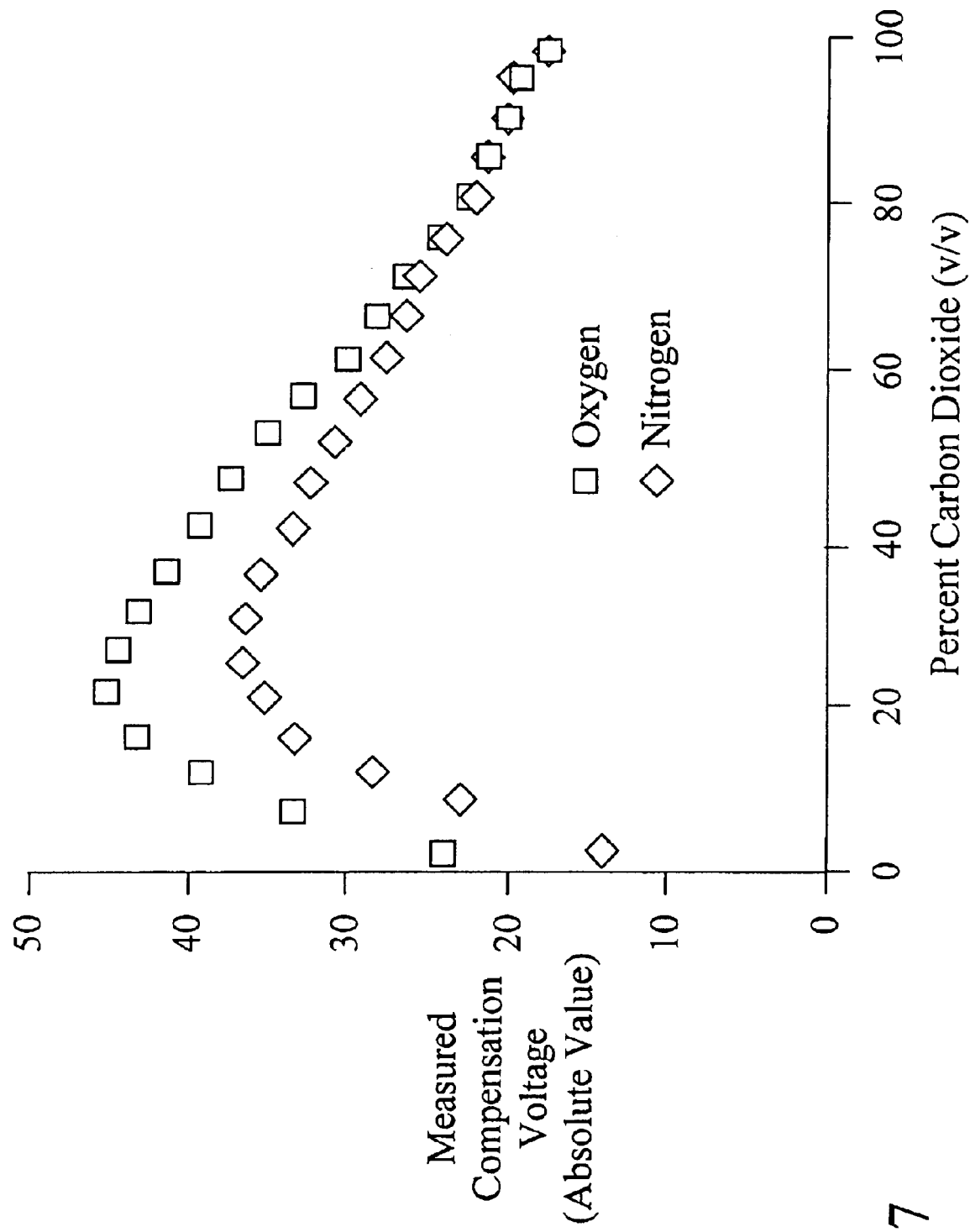
FIG. 7 shows experimental data illustrating the effect of the addition of carbon dioxide on the CV spectrum of $Cs^+$ in various bath gases.

Referring to FIG. 7, shown is a plot of the experimental data for measurements of the absolute values of CV for transmission of the positively charged $Cs^+$ ion for a series of experimental conditions including various gas compositions from 0% to 100% carbon dioxide in oxygen and nitrogen. The applied DV is 3300 volts, such that the FAIMS is operating in P1 mode. In each case carbon dioxide is added to the pure gas until the carrier gas is pure carbon dioxide. Clearly, both traces coincide on the right side of the figure, which is pure carbon dioxide carrier gas. This experiment was repeated starting with pure gases oxygen and nitrogen. At a gas mixture of about 30% carbon dioxide in oxygen, the CV of cesium ion is about 43 volts. This optimum transmission of $Cs^+$ ion occurs at CV values very significantly higher than the approximately 24 volts in pure oxygen, or the approximately 17 volts in pure carbon dioxide. The experimental data shown in FIG. 7 illustrates that at gas compositions of about 30% carbon dioxide, the $Cs^+$ ion is transmitted near 35 volts for nitrogen. At the right hand axis of FIG. 7, both traces coincide because the bath gas has been converted to pure 100% carbon dioxide.

Figure 8A:
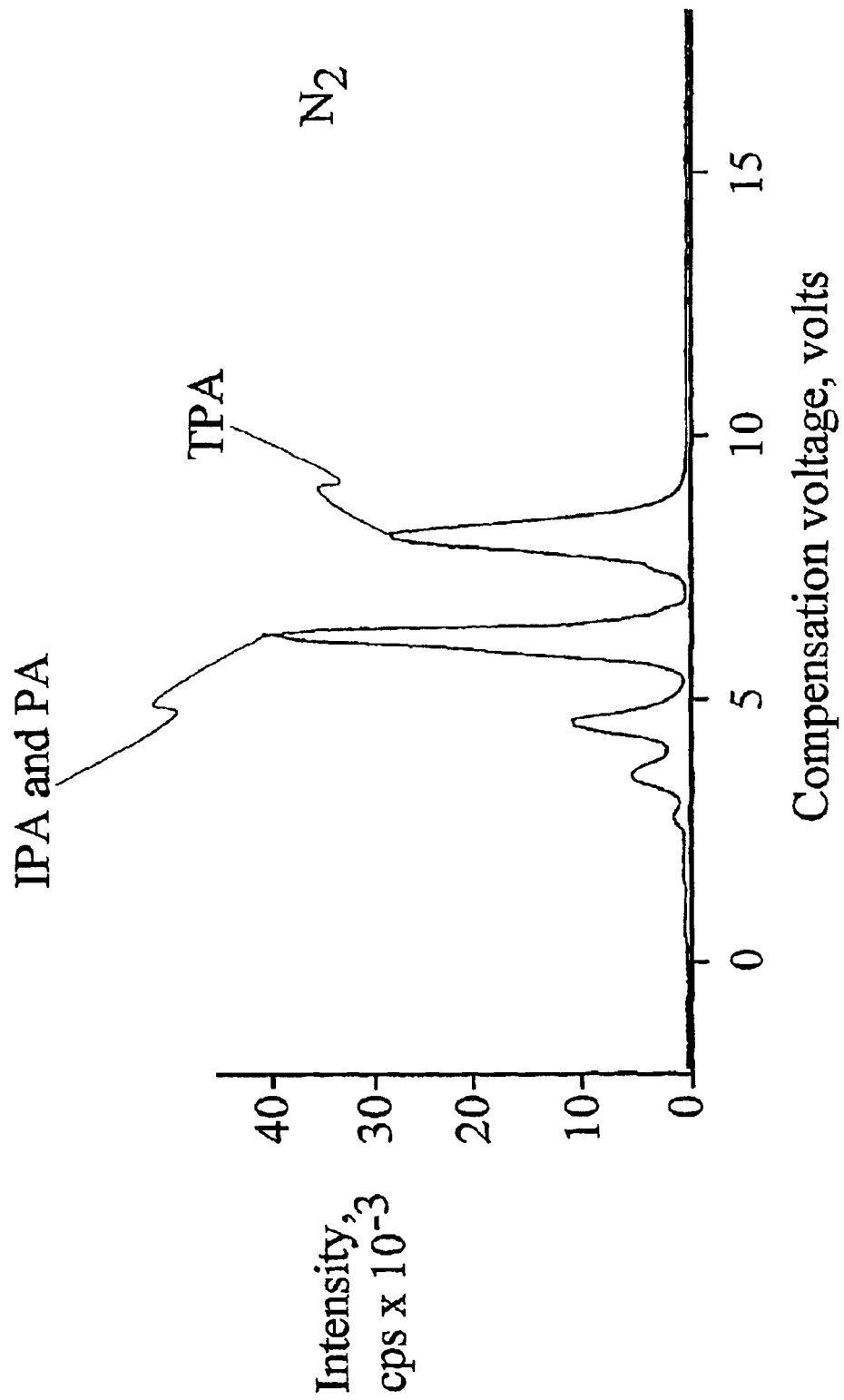
FIG. 8a shows a CV spectrum obtained from a mixture of phthalic acid (PA), isophthalic acid (IPA) and terephthalic acid (TPA) using pure nitrogen bath gas in FAIMS.
Figure 8B:
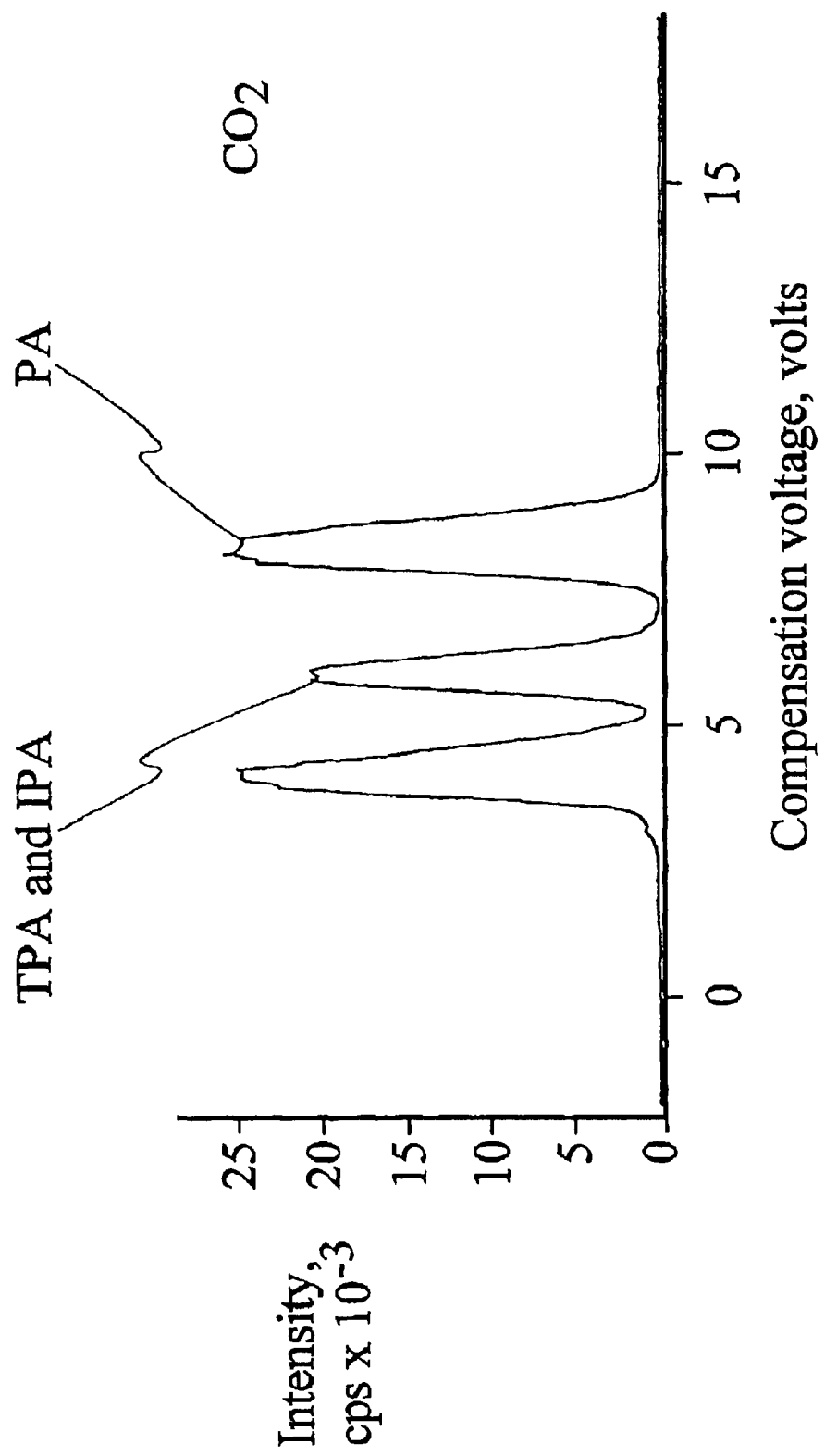
FIG. 8b shows a CV spectrum obtained from a mixture of phthalic acid (PA), isophthalic acid (IPA) and terephthalic acid (TPA) using pure carbon dioxide bath gas in FAIMS.
Figure 8C:
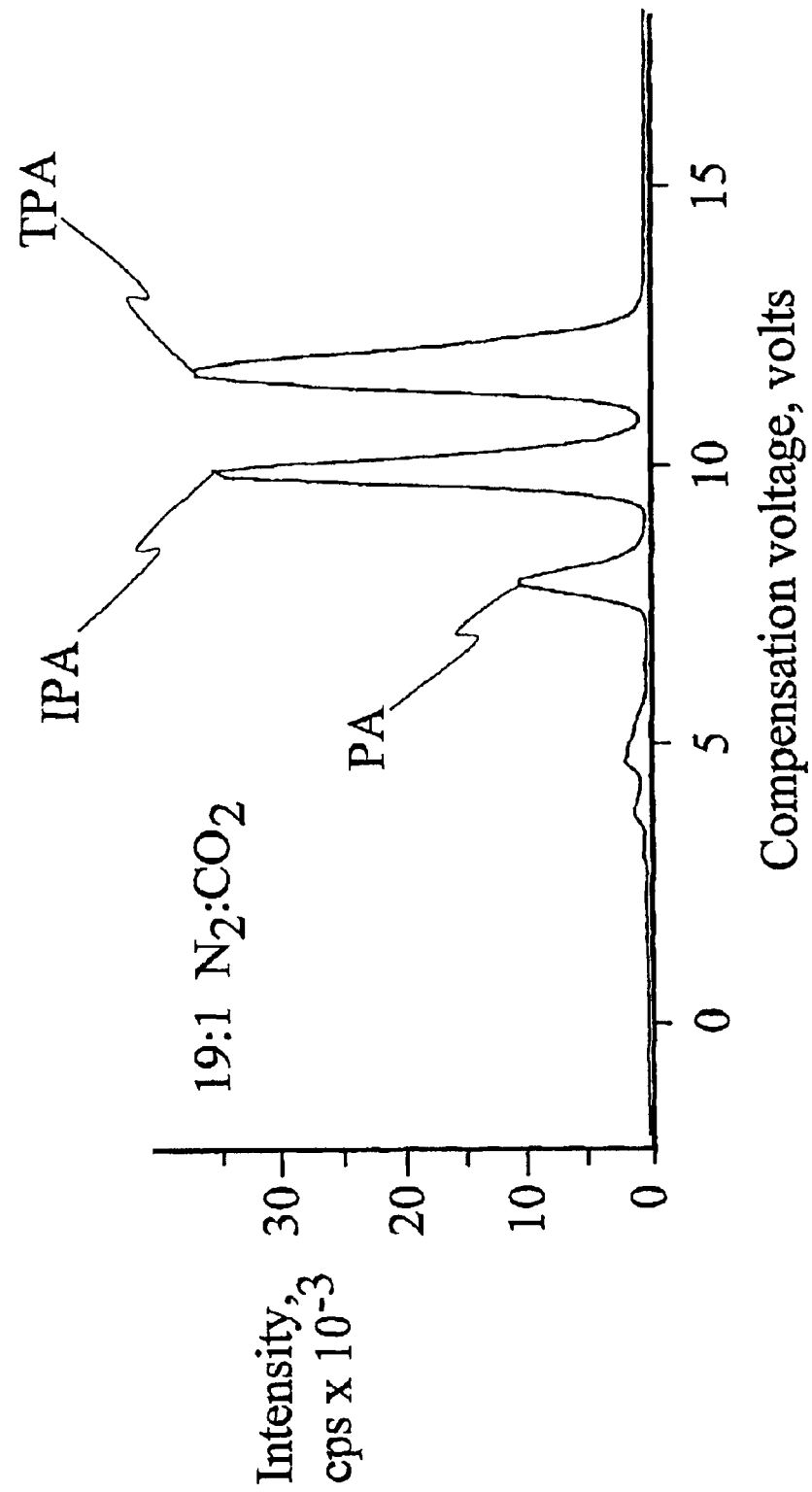
FIG. 8c shows a CV spectrum obtained from a mixture of phthalic acid (PA); isophthalic acid (IPA) and terephthalic acid (TPA) using a 19:1 mixture of nitrogen and carbon dioxide bath gas in FAIMS.

Referring to FIGS. 8a, 8b and 8c, shown are experimental results illustrating the application of mixed gases for analysis using FAIMS. Three isomers, phthalic acid (PA), isophthalic acid (IPA) and terephthalic acid (TPA), each isomer having a molecular weight of approximately 166.2 g/mol and each isomer capable of being ionized in an electrospray ionization source to produce deprotonated molecular ions in the gas phase with a mass-to-charge ratio (m/z) of 165.2. These three species cannot be separated by mass spectrometry alone. As shown in FIG. 8a, the pseudomolecular ion of terephthalic acid is separated from the other two pseudomolecular ions using ESI-FAIMS-MS with pure nitrogen carrier gas in the FAIMS. The CV spectrum appearing in FIG. 8a was obtained by monitoring the transmitted ions extracted from the FAIMS for ions of m/z −165.2. The non-labeled peaks appearing in FIG. 8a are attributed to adduct ions of phthalic acid that travel through the FAIMS intact, but are fragmented in the mass spectrometer to produce a fragment of m/z −165.2, for instance by loss of the adduct to give the original phthalic acid ion.

The CV spectrum shown in FIG. 8b is obtained under the same conditions as described with reference to FIG. 8a, except that the carrier gas is changed to pure carbon dioxide. Referring to FIG. 8b, a different isomer, phthalic acid, is resolved from the other two isomers when the carrier gas is changed to pure carbon dioxide. Of course, using either pure gas, for instance nitrogen or carbon dioxide, it is other than possible to resolve separate peaks for each of the three isomers using FAIMS. Advantageously, by using a mixture of the two gases, for instance approximately 19:1 of $N_2$ to $CO_2$, all three isomers are readily resolved, as shown with reference to the CV spectrum presented in FIG. 8c. This example illustrates that different combinations of mixed gases have profound and unpredictable effects on the separation of ions in FAIMS. The possible applications for isomer separations using FAIMS have been greatly enhanced by the discovery of the unexpected behavior of ions in these gas mixtures.

Figure 9A:
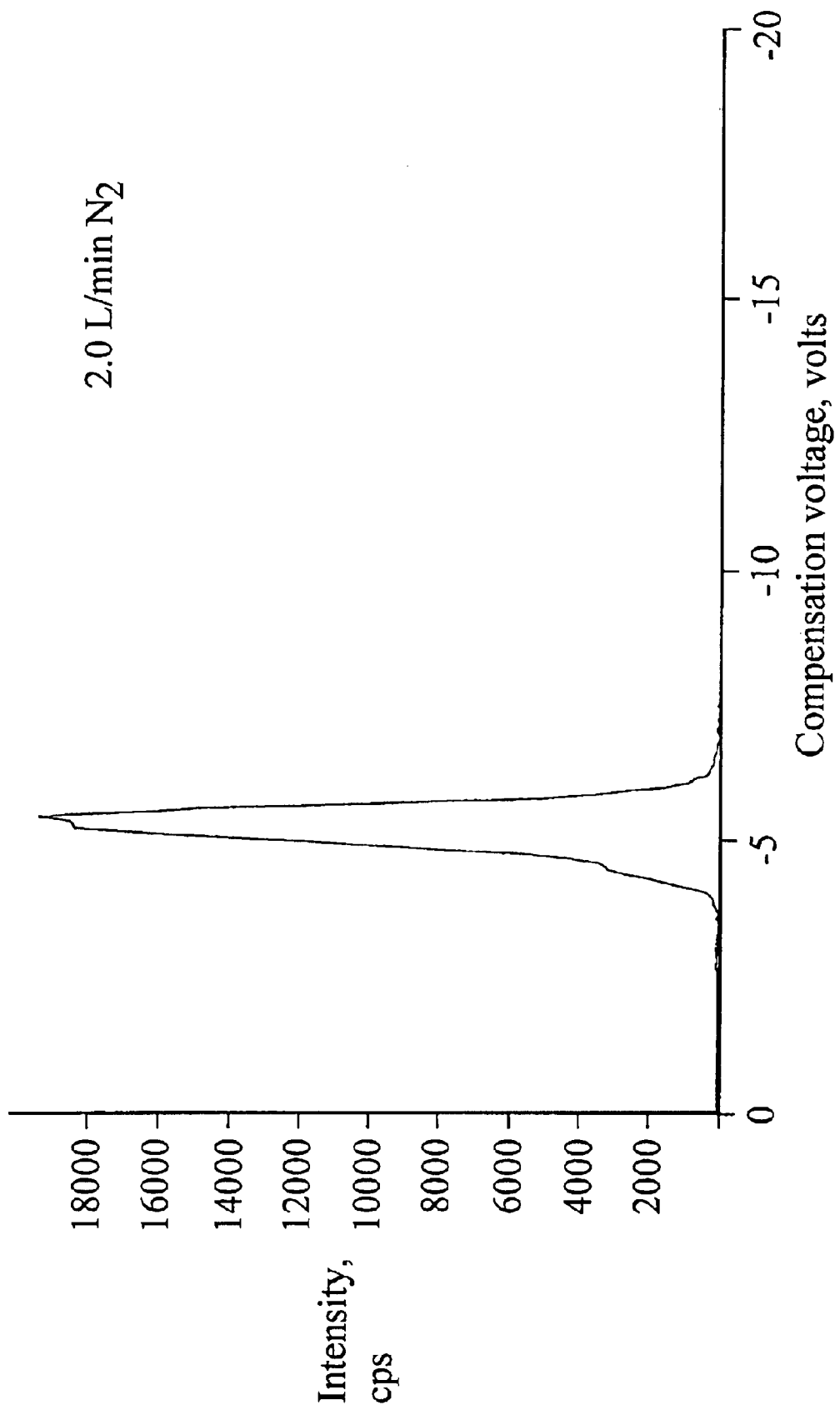
FIG. 9a show a CV spectrum obtained from a sample of the peptide bradykinin using pure nitrogen bath gas in FAIMS.
Figure 9B:
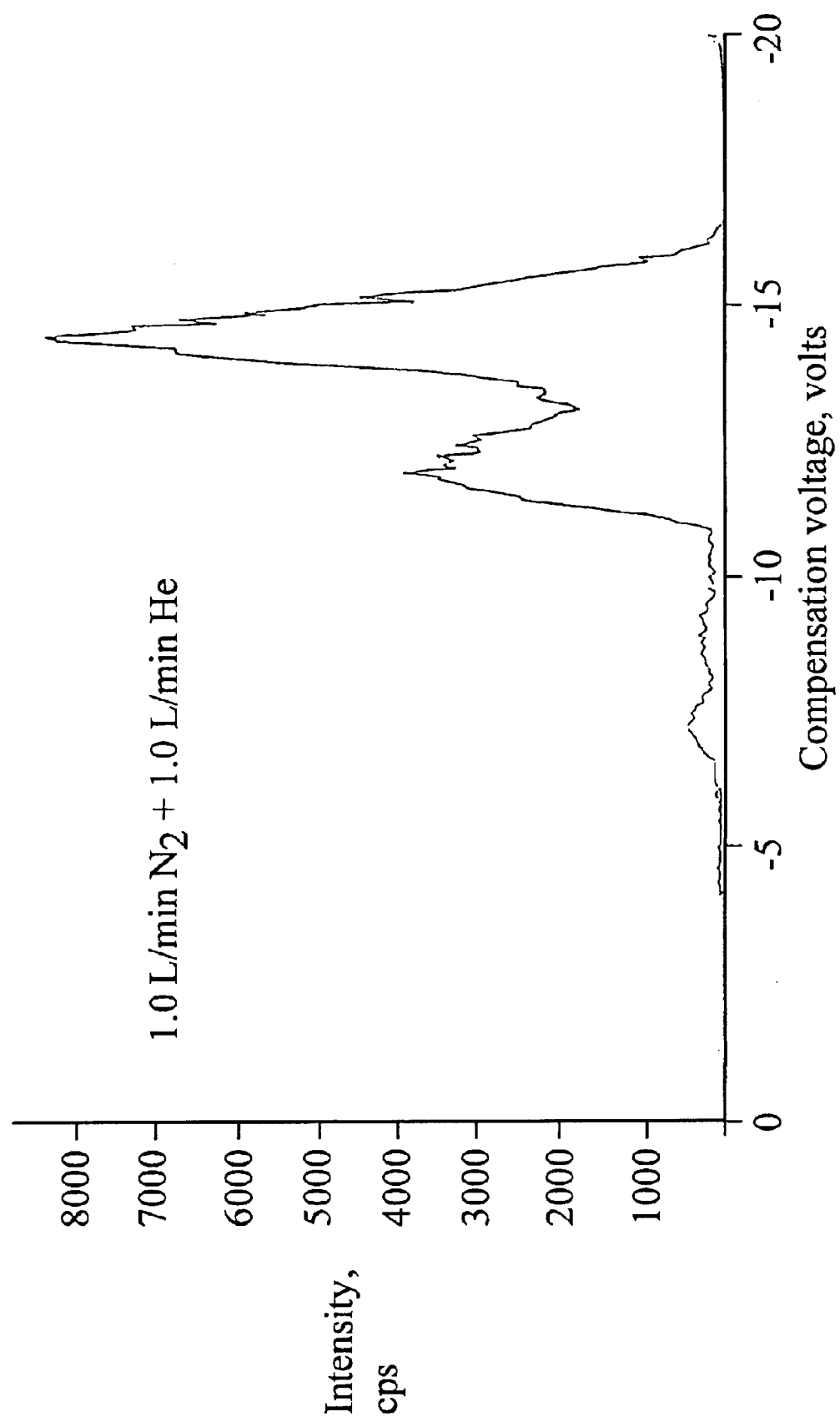
FIG. 9b show a CV spectrum obtained from a sample of the peptide bradykinin using a 1:1 mixture of nitrogen and helium bath gas in FAIMS.

Referring to FIGS. 9a and 9b, shown are experimental results illustrating the application of mixed gases for analysis of larger ions, including peptides and proteins, using FAIMS. Referring to FIG. 9a, shown is a CV spectrum, obtained for the [M+2H]$^{2+}$ ion of the peptide bradykinin by monitoring m/z 531, that is collected using pure nitrogen carrier gas in FAIMS. Although a very small shoulder is visible, a single peak dominates the spectrum. The CV spectrum that is presented in FIG. 9b is obtained using identical conditions except that the carrier gas in FAIMS is changed to a 1:1 mixture of nitrogen and helium. In this CV spectrum, the two species, both with m/z 531, are resolved separately.

Figure 10A:
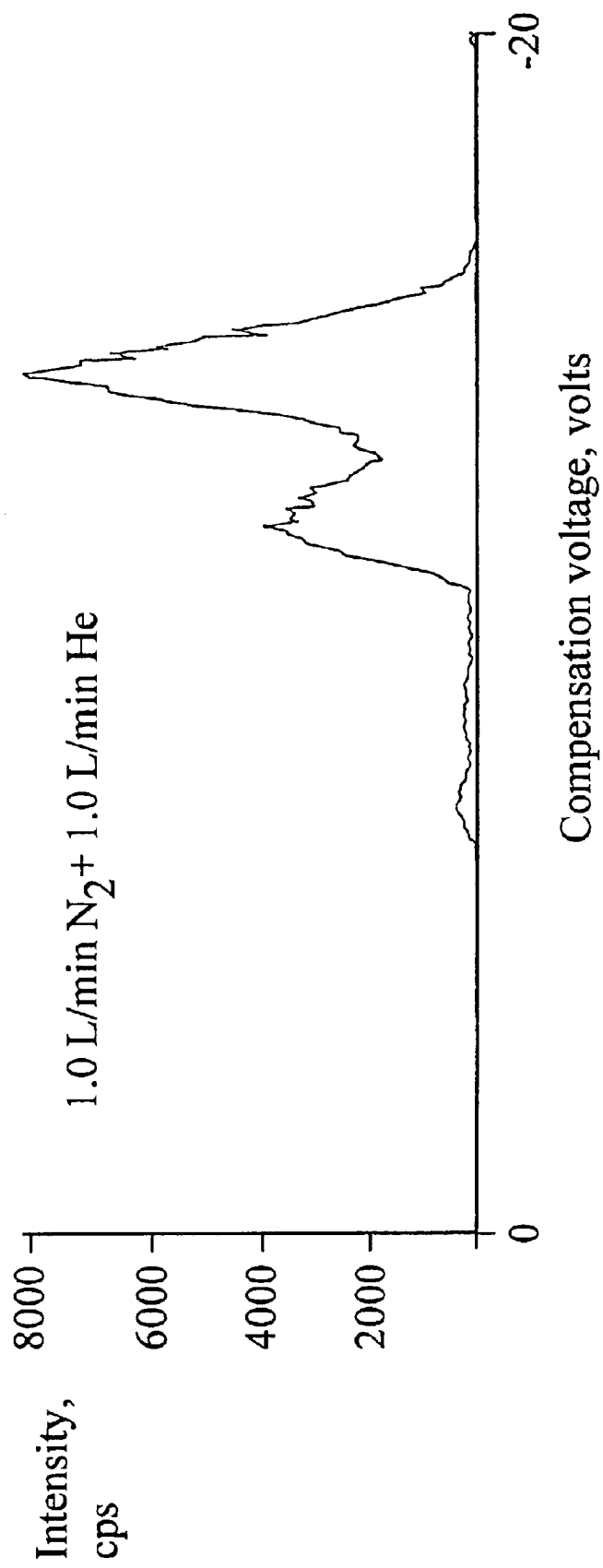
FIG. 10a show the CV spectrum presented in FIG. 9b.
Figure 10B:
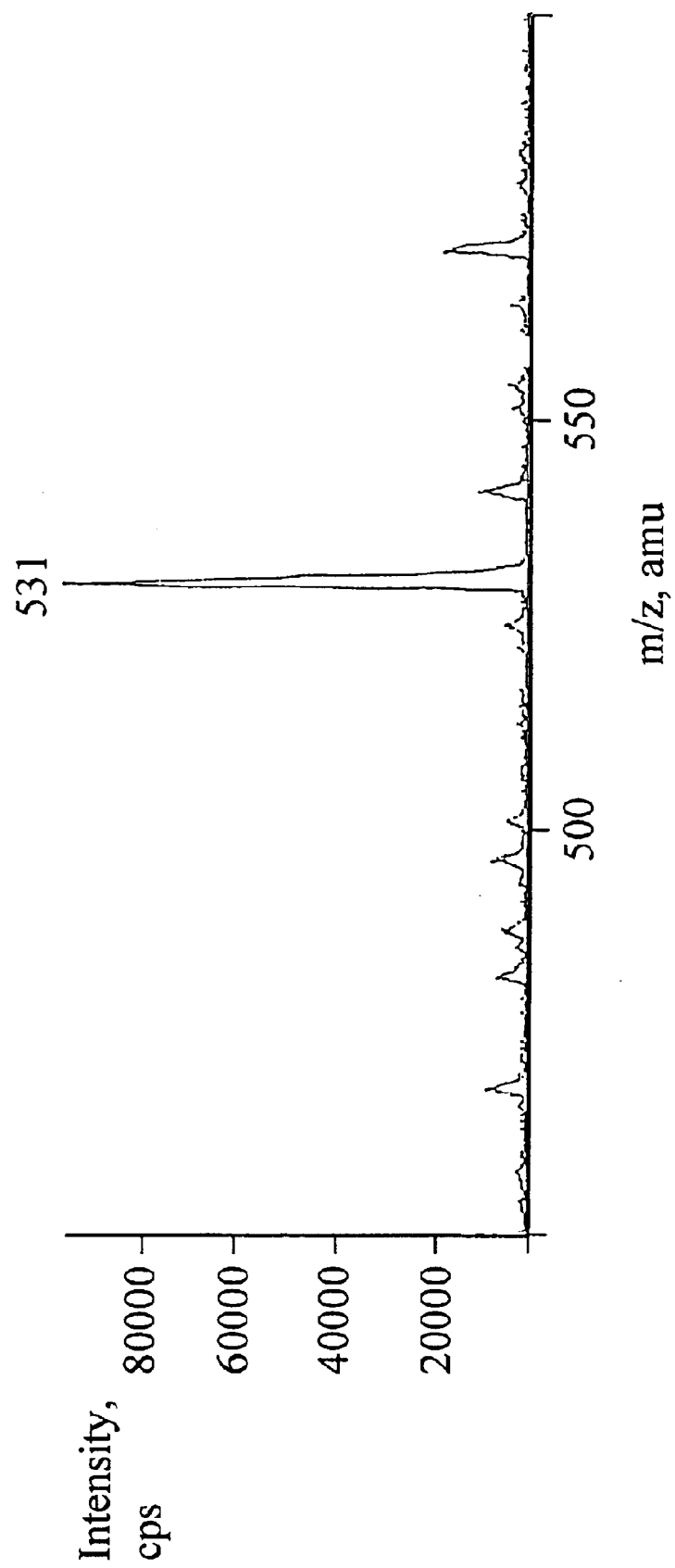
Figure 10C:
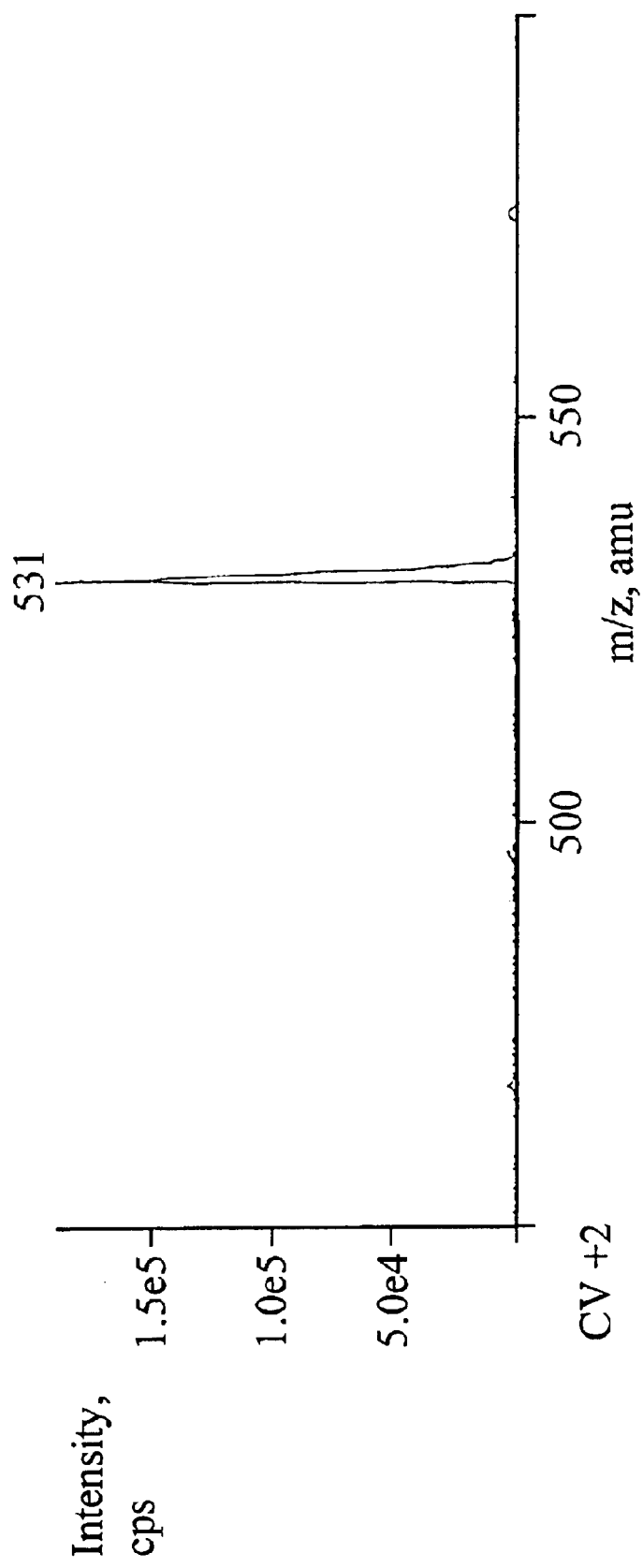

Referring to FIG. 10a, the CV spectrum of FIG. 9b is reproduced in order to facilitate the following discussion. The mass spectrum shown in FIG. 10b corresponds to the ions that are selectively transmitted at a CV of −12.3V in a 1:1 mixture of nitrogen and helium. The mass spectrum shown in FIG. 10c corresponds to the ions that are selectively transmitted at a CV of −15.5V in a 1:1 mixture of nitrogen and helium. The two mass spectra are similar to each other, suggesting that the two peaks in the CV spectrum represent different conformers of the [M+2H]$^{2+}$ ion of the peptide bradykinin. As disclosed in a copending PCT application in the name of R. Guevremont, R. Purves and D. Barnett, separation of conformers of proteins is achieved using FAIMS, however, the separation of bradykinin using mixed gases in FAIMS is unexpected and unpredictable from the behavior of the [M+2H]$^{2+}$ bradykinin ion, and other ions, in pure gases. The reason that these mixed gases improve the separation of these larger species is presently unknown, however, it is apparent that the use of mixed gases leads to separation of conformers that are otherwise unresolved from each other using a pure carrier gas in FAIMS.

Advantageously, the use of a mixture of gases make separation of certain ions feasible on the basis of the FAIMS principle, where the separation is other than possible with the normal selection of pure gases. This greatly extends the practical usefulness of FAIMS. This also greatly extends the possible effort that that can be expended to get separation of analyte ions of interest, for instance the search for the 'magic bullet' to perform a separation. Further advantageously, the FAIMS improvements described according to the present invention are readily incorporated into the existing FAIMS devices, since an external mixing chamber is optionally provided for producing the mixed gas. Further optionally, for instance in field applications using portable FAIMS devices, the gas mixture is provided by a single canister, the gaseous contents of the canister having a predetermined composition selected in dependence upon a particular field application.

Of course, numerous other embodiments could be envisioned, without departing significantly from the teachings of the present invention.

What is claimed is:

1. An apparatus for separating ions comprising:
 a high field asymmetric waveform ion mobility spectrometer, including;
  an analyzer region comprising two electrodes, for providing an electric field therebetween resulting from an application of an asymmetric waveform to at least one of the two electrodes in order to affect ion mobility, and for allowing at least a gas to pass therebetween;
  at least a gas inlet for introducing a first gas and a second other gas into the analyzer region, each one of the first gas and the second other gas being other than ions; and, a mixing chamber disposed between the at least a gas inlet and a first gas source and a second gas source, the mixing chamber in fluid communication with the at least a gas inlet, the first gas source and the second gas source for, in use, receiving a flow of the first gas from the first gas source and a flow of the second other gas from the second gas source, the mixing chamber for providing a flow of a carrier gas having a predetermined composition, other than substantially a same composition as air, including the first gas and the second other gas, to the at least a gas inlet for introduction into the analyzer region.

2. An apparatus according to claim 1 wherein the mixing chamber is a gas manifold disposed external to the analyzer region.

3. An apparatus for separating ions comprising:
 a high field asymmetric waveform ion mobility spectrometer, including;
  an analyzer region comprising two electrodes, for providing an electric field therebetween resulting from an application of an asymmetric waveform to at least one of the two electrodes in order to affect ion mobility, and for allowing at least a gas to pass therebetween;
  at least a gas inlet for introducing a first gas and a second other gas into the analyzer region, each one of the first gas and the second other gas being other than ions,
 wherein, in use, the at least a gas inlet is in fluid communication with a source of a mixed gas, the mixed gas having a predetermined composition, other than substantially a same composition as air, including the first gas and the second other gas.

4. An apparatus for separating ions comprising:
 a high field asymmetric waveform ion mobility spectrometer, including;
 an analyzer region comprising two electrodes, for providing an electric field therebetween resulting from an application of an asymmetric waveform to at least one of the electrodes in order to affect ion mobility, and for allowing at least a gas to pass therebetween;
 a first gas inlet in fluid communication with a first gas source for receiving a flow of a first gas therefrom, the first gas being other than ions; and,
 a second gas inlet in fluid communication with a second gas source for receiving a flow of a second other gas therefrom, the second other gas being other than ions, and,
 a mixing chamber disposed between the first and second gas inlets and the analyzer region, the mixing chamber separately in fluid communication with each one of the first and second gas inlets and the analyzer region for receiving a flow of the first gas from the first gas inlet and a flow of the second other gas from the second gas inlet and for providing at least a flow of a carrier gas including the first gas and the second other gas and having a predetermined composition, other than substantially a same composition as air, to the analyzer region.

5. An apparatus according to claim 4 wherein, in use, the first gas and the second other gas are selected from the group including: a pure gas; a gaseous mixture including two gaseous components other than the ions; a vapor; and, an aerosol.

6. A method for separating ions, comprising the steps of:
 a) providing two electrodes including a first electrode and a second electrode;
 b) providing an asymmetric waveform and a direct-current compensation voltage, to at least one of the two electrodes to form an electric field therebetween, the field for effecting a difference in net displacement between ions in a time of one cycle of the applied asymmetric waveform for effecting a separation of the ions by forming a subset thereof;

c) determining a carrier gas composition, other than substantially a same composition as air, including at least two different chemical components other than ions, for effecting a separation of ions having approximately similar high field mobility properties in a pure carrier gas absent one of the at least two different chemical components;

d) providing through the electric field a flow of a carrier gas having the determined composition and including at least two different chemical components; and, e) transporting ions through the electric field in a direction approximately transverse to the electric field, wherein the two different chemical components act in conjunction with the electric field to effect a separation of the ions having approximately similar high field mobility properties in a pure carrier gas absent one of the at least two different chemical components.

7. A method according to claim 6, including the additional steps of:

a1) providing an analyzer region defined by a space between the two electrodes, the analyzer region having at least one each of a gas inlet and a gas outlet, the gas inlet for introducing a flow of the carrier gas through the analyzer region and out of the gas outlet, the analyzer region having an ion inlet and an ion outlet, the ion inlet for introducing ions into the analyzer region, and the ion outlet for providing ions from the analyzer region.

8. A method according to claim 7, wherein step (c) comprises the steps of:

varying the carrier gas composition; and, varying the compensation voltage and measuring resulting selectively transmitted ions to produce a compensation voltage scan for the selectively transmitted ions.

9. A method according to claim 8 wherein step e) includes the step of providing ions from at least one ionization source.

10. A method according to claim 9 including the step of detecting said selectively transmitted ions by mass spectrometry.

11. A method according to claim 10 wherein the ions are transported through the analyzer region by the carrier gas.

12. A method according to claim 11, including the step of providing a source of a premixed carrier gas including at least two different predetermined chemical components, for providing the carrier gas having a predetermined composition.

13. A method according to claim 12 wherein the predetermined chemical components are selected from the group consisting of a pure gas; a gaseous mixture including two gaseous components other than the ions; a vapor; and, an aerosol.

14. A method according to claim 6 wherein the predetermined chemical components are selected from the group consisting of a pure gas; a gaseous mixture including two gaseous components other than the ions; a vapor; and, an aerosol.

15. An apparatus for separating ions comprising:

a high field asymmetric waveform ion mobility spectrometer, including; an analyzer region comprising two electrodes for providing an electric field therebetween resulting from an application of an asymmetric waveform to at least one of the two electrodes in order to affect ion mobility, and for allowing at least a gas to pass therebetween; and, a gas inlet; and, a mixing chamber disposed between the gas inlet and a first and a second gas source, the mixing chamber including a first gas flow adjuster for providing a controllably variable flow of a first gas from the first gas source to the mixing chamber and a second gas flow adjuster for providing a controllably variable flow of a second gas from the second gas source to the mixing chamber, the controllably variable flow of the first gas and the controllably variable flow of the second gas for forming a mixed carrier gas having a predetermined composition, other than substantially a same composition as air, for being introduced into the analyzer region via the gas inlet.

16. An apparatus according to claim 15, wherein the mixing chamber is a gas manifold disposed external to the analyzer region.

17. An apparatus according to claim 16, wherein the first gas flow adjustor is a first valve and wherein the second gas flow adjustor is a second valve.

18. An apparatus according to claim 17, wherein the first valve and the second valve are electronically actuatable.

19. An apparatus according to claim 17, wherein the first valve and the second valve are manually actuatable.

* * * * *